(12) United States Patent
Bogdanoff et al.

(10) Patent No.: US 12,000,852 B2
(45) Date of Patent: Jun. 4, 2024

(54) APPARATUS AND METHOD FOR ISOLATING SINGLE PARTICLES FROM A PARTICLE SUSPENSION

(71) Applicants: SCIENION GMBH, Berlin (DE); The Regents of the University of California, Oakland, CA (US)

(72) Inventors: Derek Bogdanoff, San Francisco, CA (US); Eric Chow, El Cerrito, CA (US); Michael Wilson, Moraga, CA (US); Ariele Lauren Greenfield, San Francisco, CA (US); Joshua Cantlon-Bruce, Berkeley, CA (US)

(73) Assignees: SCIENION GMBH, Berlin (DE); The Regents of the University of California, Oakland, CA (US)

( * ) Notice: Subject to any disclaimer, the term of this patent is extended or adjusted under 35 U.S.C. 154(b) by 1159 days.

(21) Appl. No.: 16/518,495

(22) Filed: Jul. 22, 2019

(65) Prior Publication Data

US 2020/0025783 A1 Jan. 23, 2020

(30) Foreign Application Priority Data

Jul. 23, 2018 (EP) .................................... 18185007

(51) Int. Cl.
*G01N 35/10* (2006.01)
*B01L 3/02* (2006.01)
(Continued)

(52) U.S. Cl.
CPC .......... *G01N 35/1009* (2013.01); *B01L 3/021* (2013.01); *B01L 3/0265* (2013.01);
(Continued)

(58) Field of Classification Search
None
See application file for complete search history.

(56) References Cited

U.S. PATENT DOCUMENTS 5,308,757 A 5/1994 Kawamura et al.
7,736,591 B2 6/2010 Rose et al.
(Continued)

FOREIGN PATENT DOCUMENTS

CN 1315913 A 10/2001
CN 104321634 A 1/2015
(Continued)

OTHER PUBLICATIONS

Chen et al., "Rare cell isolation and analysis in microfluids", Lab Chip., vol. 14, No. 4, pp. 626-645 (2014).
(Continued)

*Primary Examiner* — Matthew D Krcha
*Assistant Examiner* — Brittany I Fisher
(74) *Attorney, Agent, or Firm* — Caesar Rivise, PC (57) ABSTRACT

A particle isolation apparatus 100 for isolating particles from a suspension sample, includes a droplet dispenser device 10 for collecting the suspension sample from a carrier substrate 20 and for dispensing droplets onto a target substrate 30, a mechanical pump device 40 being coupled with the droplet dispenser device 10 for loading a dilution liquid into the droplet dispenser device 10 and for aspirating a first portion of the suspension sample into the droplet dispenser device 10, and a syphon pump device 50 being coupled with the droplet dispenser device 10 and being arranged for aspirating a second portion of the suspension sample into the droplet dispenser device 10. Preferably, the droplet dispenser device 10 is configured for dispensing single particle droplets on the target substrate 30. Furthermore, a method of isolating particles from a suspension sample is described.

14 Claims, 5 Drawing Sheets

(51) Int. Cl.
*C12M 1/00* (2006.01)
*G01N 1/28* (2006.01)
*G01N 1/38* (2006.01)

(52) U.S. Cl.
CPC .......... *C12M 47/04* (2013.01); *B01L 2400/04* (2013.01); *B01L 2400/0622* (2013.01); *G01N 2035/1034* (2013.01); *G01N 2035/1058* (2013.01)

(56) References Cited

U.S. PATENT DOCUMENTS

| | | |
|---|---|---|
| 9,269,138 B2 | 2/2016 | Zahniser et al. |
| 2002/0001675 A1 | 1/2002 | Tisone |
| 2002/0064482 A1 | 5/2002 | Tisone et al. |
| 2005/0003458 A1* | 1/2005 | Moore ............... G01N 35/1016 435/325 |
| 2008/0296157 A1 | 12/2008 | Bauer et al. |
| 2013/0095469 A1* | 4/2013 | Koltay ................ C12M 41/48 435/286.4 |
| 2014/0065704 A1 | 3/2014 | Shirai et al. |
| 2017/0274689 A1 | 9/2017 | Rodriguez et al. |
| 2018/0056294 A1 | 3/2018 | Di Carlo et al. |

FOREIGN PATENT DOCUMENTS

| | | |
|---|---|---|
| CN | 104541146 A | 4/2015 |
| EP | 3323877 A1 | 5/2018 |
| JP | H04-094696 A | 3/1992 |
| JP | 2012-217397 A | 11/2012 |
| WO | 03022438 A1 | 3/2003 |
| WO | 2013155288 A1 | 10/2013 |

OTHER PUBLICATIONS

Masuda et al., "Rare cell isolation and recovery on open-channel microfluidic chip", PLoS ONE 12(4): e0174937. https://doi.org/10.1371/journal.pone.0174937.

European Search Report for application EP 18185007 dated Dec. 19, 2018.

Office Action re JP 2019-133325 (dated May 9, 2023).

CNIPA, Office Action re CN App. No. 201910665596.X (dated Oct. 27, 2023).

* cited by examiner

APPARATUS AND METHOD FOR ISOLATING SINGLE PARTICLES FROM A PARTICLE SUSPENSION

TECHNICAL FIELD

The present invention relates to a particle isolation apparatus, which is configured for isolating particles, in particular biological cells, cell aggregates, cell components or biological macromolecules, from a particle suspension sample. Furthermore, the invention relates to a method of isolating particles from a particle suspension sample. Applications of the invention are available in the field of processing particle suspensions, like biological samples, in particular for handling and recovery of single biological cells or cell subpopulations, e. g. for culturing or molecular analyses purposes.

TECHNICAL BACKGROUND

In the fields of biochemistry and biomedicine, there is an interest in identifying rare cells in a larger population of background cells, e.g. for identifying specific cells in a blood sample, which indicate a disease (like tumor cells) or which are useful for further cell processing. Generally, identifying cells in a cell mixture, like a cell suspension, comprises a first step of isolating the cells from each other and a second step of analyzing the single cells.

A common technique of isolating cells is based on existing droplet spotting techniques, wherein a droplet dispenser is utilized for handling suspension droplets. Droplets of a cell suspension are aspirated from a well structure into a droplet dispenser, so that a dilution in a buffer liquid in the droplet dispenser is obtained. Subsequently, droplets including single cells are deposited onto a target for the subsequent analysis of the single cells and further processing. However, as a disadvantage, those techniques have low rates of cell recovery, e. g. in a range from 5% to 60%, making them impractical for working with paucicellular biological samples. For isolating single cells from a cell suspension, including e.g. less than 1000 cells per ml, recovery rates above 90% are required. EP 3 323 877 A1 and US 2002/001675 A1 disclose droplet dispensing techniques wherein an aspirating action of a syphon pump is used for delivering a liquid from a reservoir to a droplet dispenser. However, these conventional configurations are not capable of increasing the recovery rates.

As an alternative to spotting techniques, microfluidic systems have been used for rare cell isolation and analysis. A liquid suspension including biological cells flows through a microfluidic system, wherein cells are isolated from each other by flowing the suspension through a narrow channel and forming a row of individual cells. Subsequently, the single cells are analyzed and sorted in dependency on the occurrence of cellular biomarkers, specific physical properties or dielectric properties. A summary of the microfluidics techniques for rare cell isolation is presented by Y. Chen et al. in "Lab Chip", 2014, 14(4), 626-645. A particular example of a microfluidics technique utilizing an open-channel microfluidic chip is described by T. Masuda et al. in "PLOS One", 2017, 12(4), e 0174937.

Microfluidics techniques have an advantage in terms of a high recovery rate as cell loss is minimized. However, a disadvantage results from the fact that cell handling in the channels of the microfluidic system can change the cells. Furthermore, microfluidic systems are complex devices, which have to be able to detect specific cell signatures, like e. g. a hydrodynamic signature (size, density or deformability), a dielectrophoretic signature (specific membrane capacities), an immune chemical signature (specific antibodies) or a magnetophoretic signature (magnetic susceptibility or immune specific bonding to magnetic nanoparticles). Microfluidic systems can be integrated in available droplet processing methods in a restricted manner only.

The above limitations of conventional techniques do not occur only with regard to single cell isolation, but correspondingly also with other particle separation techniques, e. g. for separating other types of biological particles or non-biological particles, like in environmental investigations.

OBJECTIVE OF THE INVENTION

The objective of the invention is to provide an improved particle isolation apparatus, which is capable of isolating particles from a suspension sample, avoiding the disadvantages and limitations of conventional techniques. In particular, the particle isolation apparatus is to be capable of isolating particles with an increased recovery rate, with a high-throughput capability and/or with a simple integration into available droplet processing methods. Furthermore, the objective of the invention is to provide an improved method of isolating particles from suspension sample, avoiding the disadvantages and limitations of conventional techniques.

SUMMARY OF THE INVENTION

The above objectives are respectively solved by a particle isolation apparatus and a method of isolating particles from a suspension sample, comprising the features of the independent claims. Features of preferred embodiments and applications of the inventions are defined in the dependent claims.

According to a first general aspect of the invention, the above objective is solved by a particle isolation apparatus, comprising a combination of a droplet dispenser device with a mechanical pump device and a syphon pump device. The droplet dispenser device comprises at least one droplet dispenser, like e.g. at least one piezoelectric droplet dispenser. The droplet dispenser device is arranged for collecting suspension sample from a carrier substrate and for dispensing droplets into a target substrate. The suspension sample comprises a quantity of liquid including a plurality of particles, like biological cells. The suspension sample can be provided as a droplet on a carrier substrate surface or as the content of a compartment, like a 3D well, of the carrier substrate. The droplet dispenser device is configured for collecting the suspension sample into the at least one droplet dispenser by the effect of a negative pressure, preferably through a droplet dispenser tip of the least one droplet dispenser. The negative pressure is applied by the mechanical pump device or the syphon pump device.

The mechanical pump device is coupled with the droplet dispenser device, preferably via an upper droplet dispenser junction. The mechanical pump device is configured for loading an incompressible dilution liquid, like i.e. a buffer liquid, into the droplet dispenser device. Furthermore, the mechanical pump device is configured for aspirating a first portion of the suspension sample by the effect of a negative pressure into the droplet dispenser device. The mechanical pump device comprises any pump device, which is capable of creating a positive or negative pressure, e. g. by moving a piston in a system liquid, provided by the dilution liquid, or a peristaltic pump. The mechanical pump device is operated with a system liquid, which comprises the dilution liquid or another liquid, like pure water.

According to the invention, the syphon pump device additionally is coupled with the droplet dispenser device, preferably with the upper droplet dispenser junction of the at least one droplet dispenser. The syphon pump device is arranged for aspirating a second portion of the suspension sample by the effect of a negative pressure into the droplet dispenser device. The syphon pump device is operated with a system liquid, which comprises the dilution liquid or another liquid, like pure water. Preferably, the syphon pump device and the mechanical pump device employ the same system liquid.

According to a second general aspect of the invention, the above objective is solved by a method of isolating particles from a suspension sample, comprising the following steps. With a preparation of the isolating method, the suspension sample is provided on a carrier substrate, like a plane substrate surface or a compartment of a 3D well structure. Furthermore, a dilution liquid, i.e. a buffer liquid, is loaded to at least one droplet dispenser of a droplet dispenser device. For isolating single particles from the suspension sample, the suspension sample is loaded to the droplet dispenser device such that the suspension sample is diluted in the dilution liquid. The dilution in the dilution liquid comprises two aspiration phases. In a first aspiration phase, a first portion of the suspension sample is drawn into the droplet dispenser device, in particular into the at least one droplet dispenser, by the action of a mechanical pump device. In a second aspiration phase, a second portion, in particular the remaining suspension sample, is aspirated into the droplet dispenser device, in particular into the at least droplet dispenser, by the action of a syphon pump device. The aspirating of the suspension sample results in a dilution of the suspension sample within the at least one droplet dispenser. Finally, the droplet dispenser device can be operated, including dispensing droplets into a target substrate. The target substrate may comprise another portion of the carrier substrate or another substrate separated from the carrier substrate. Droplets of the diluted suspension sample are dispensed as free droplets onto a plane target substrate surface or into 3D wells of the target substrate. The droplet dispenser device is operated such that the droplets dispensed onto the target substrate include less than one particle per droplet in temporal average. In other words, the droplet dispenser device is controlled such that each droplet dispensed onto the target substrate includes one single particle or no particle. Droplets potentially including more than one particle are not dispensed onto the target substrate.

As a main advantage, by employing the syphon pump device for aspirating liquid into the droplet dispenser device, the recovery rate of isolating particles can be increased compared with the conventional techniques. Recovery rates above 90% have been obtained as dead volumes are excluded or incomplete sample collection is excluded. The syphon pump device is effective as long as a remaining portion of the liquid suspension sample is present on the carrier substrate. Thus, according to an advantageous embodiment of the invention, the suspension sample can be collected from the carrier substrate in a residue-free manner. As a further advantage, the invention allows an integration of the particle isolation into the high throughput process. Furthermore, due to the use of the droplet dispenser device, advantages in terms of combining the inventive technique with droplet handling and processing techniques are obtained.

Contrary to the conventional microfluidics techniques, the particles are not sorted in dependency on a specific signature, but by the dilution of the suspension sample in the droplet dispenser and the operation of the droplet dispenser such that single particle droplets are disposed on the target substrate. Advantageously, the particle isolation does not require a detection of specific particle features, so that the particle isolation apparatus can be used for isolating different types of particles from the suspension sample or from different suspension samples.

Preferably, the droplet dispenser device of the inventive particle isolation apparatus is configured for a single particle droplet dispensing operation. The droplet dispenser is configured such that it can be operated for dispensing droplets onto a target substrate only if the droplet includes at most one particle. To this end, the droplet dispenser device preferably is combined with a camera device being arranged for monitoring a particle distribution within the at least one droplet dispenser and a dispenser control device being configured for controlling the dispensing operation in dependency on output signals of the camera device. Preferably, single particle dispensing is implemented as described in US 2017/0274689 A1 and/or EP No. 17189875.2 (not published on the priority date of the present specification).

According to a preferred embodiment of the invention, the mechanical pump device comprises a syringe pump, which is coupled with the droplet dispenser device. A syringe pump has particular advantages in applying positive or negative pressures onto small amounts of system liquids.

According to a further advantageous embodiment of the invention, the syphon pump device comprises a system liquid reservoir which is arranged at a level lower than the carrier substrate and which is coupled via a syphon line with the droplet dispenser device, preferably the upper droplet dispenser junction of the at least one droplet dispenser. Advantageously, the combination of the at least one droplet dispenser with the system liquid reservoir provides a simple set up, allowing a reliable pump action for residue-free collection of the suspension sample.

Further advantages for connecting the pump devices with the droplet dispenser device are obtained if, according to a further, particularly preferred embodiment of the invention, the particle isolation apparatus comprises a valve device. The valve device is configured for controlling liquid connections of the mechanical pump device and/or the syphon pump device with the droplet dispenser device. Preferably, only one system liquid line is connected with the upper dispenser junction of the at least one droplet dispenser. Advantageously, the valve device facilitates a connection of the pump devices with the common system liquid line.

Particular advantages for providing a compact structure are obtained if the valve device comprises a three-way valve which is arranged for providing a liquid connection either between the mechanical pump device and the droplet dispenser device or between the syphon pump device and the droplet dispenser device. By connecting the system liquid line of the at least one droplet dispenser with a first port of the three-way valve, the mechanical pump device, in particular the syringe pump, with a second port of the three-way valve and the syphon pump device, in particular the syphon line with a third port of the three-way valve, aspirating the suspension sample with the above two aspiration phases easily can be controlled.

According to a further advantageous embodiment of the invention, the carrier substrate has a hydrophobic surface. Additionally or alternatively, the carrier substrate may have a plane, smooth surface, i. e. a surface without steps or receptacles. Advantageously, the provision of the hydrophobic surface and/or the plane, smooth surface facilitates the residue-free collection of the suspension sample from the carrier substrate.

According to another advantageous modification of the invention, the particle isolation apparatus can be provided with a recovery vessel. The recovery vessel is arranged for recapturing droplets including multiple particles. Additionally, it can be arranged for recapturing droplets including no particles. Advantageously, the provision of the recovery vessel further improves the recovery rate as the recaptured liquid can be subjected to the further application of the inventive particle isolating method.

According to a further advantageous feature of the inventive method of isolating particles, an additional quantity of the dilution liquid can be loaded to the droplet dispensary device after aspirating the suspension sample, in particular after the second aspiration phase. Advantageously, a buffer zone is created in the at least one droplet dispenser between the diluted sample suspension within the droplet dispenser and the droplet dispenser tip. The buffer zone facilitates washing the dispenser tip and the single particle operation of the dispenser.

According to preferred applications of the invention, in particular in biology, medicine and biochemistry, the particles comprise biological cells, cell aggregates, cell components, biological macromolecules and/or micro-particles (beads) functionalized with biomolecules. With these applications, the dilution liquid preferably comprises a physiological buffer solution, like i.e. a physiological cultivation liquid.

The invention has the following further advantages. The invention has a broad range of applications, including providing tools for sample preparation of various "-omic"-analysis of rare cell populations from clinical samples, culturing of individual, rare immune cells for immunotherapy screening, culturing of individual, rare immune cells for in vitro studies, and/or analyses of cellular heterogeneity of organoids.

As the main advantage, the invention enables to isolate nearly 100% of cells from very limited samples to gain more representative single cell population data, including i.e. gene expression data, immunoglobulin sequences, and in vitro phenotypic data.

The inventive method can be completely automated. The particle isolation apparatus can be controlled such that the sample suspension aspiration and the single particle dispensing operation are operated automatically.

BRIEF DESCRIPTION OF THE DRAWINGS

Further advantages and details of the invention are described in the following with reference to the attached drawings, which show in.

DESCRIPTION OF PREFERRED EMBODIMENTS

Features of preferred embodiments of the invention are described in the following with exemplary reference to a particle isolation apparatus comprising a droplet dispenser device with one single piezoelectric droplet dispenser. The invention is not restricted to this embodiment. An array of droplet dispensers can be used, having advantages for implementing a parallel operation with multiple suspension samples. Furthermore, other types of droplet dispensers can be used instead of the piezoelectric droplet dispenser. Furthermore, the implementation of the invention is not restricted to the particular configuration of the pump and valve devices in the figures. In particular, the syringe pump can be replaced by another mechanical pump device, and the bottle-shaped system liquid reservoir of the syphon pump device can be replaced by another reservoir type.

The embodiments of the invention are described with exemplary reference to the processing of biological particles, in particular biological cells. The invention is not restricted to this application. Non-biological particles can be processed with the inventive technique as well, e.g. for collecting particles from a sample in nano-techniques or environmental techniques, i.e. for analyzing purposes.

The invention is substantially described with reference to the dilution of the suspension sample in the droplet dispenser. The subsequent single particle droplet dispensing operation of the droplet dispenser device is not described as it is known per se. US 2017/0274689 A1 and EP No. 17189875.2 (not published on the priority date of the present specification) are introduced into the present specification by reference, in particular with regard to the control of the droplet dispenser device for obtaining dispensing of droplets including single particles.

Figure 1:
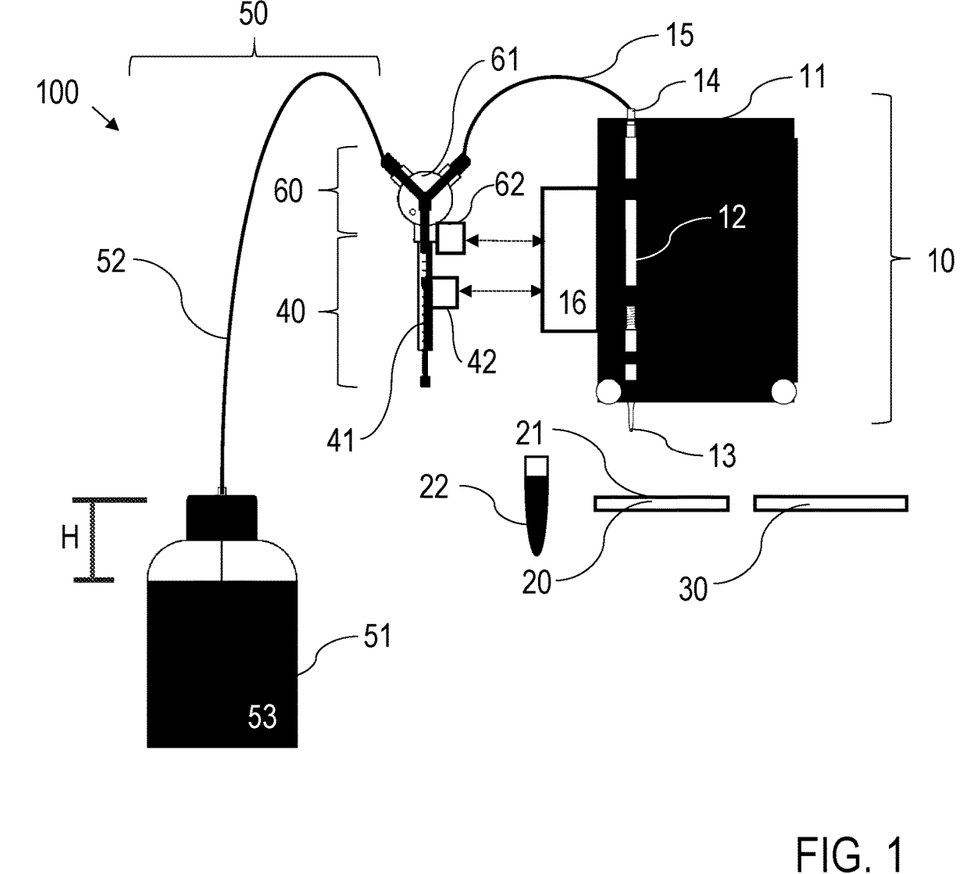
FIG. 1: a schematic illustration of a preferred embodiment of the particle isolation apparatus according to the invention.

According to FIG. 1, an embodiment of the inventive particle isolation apparatus 100 comprises a droplet dispenser device 10, a mechanical pump device 40, a syphon pump device 50 and a valve device 60. The droplet dispenser device 10 is i.e. a dispenser system of the type sciFLEXARRAYER (manufacturer: Scienion AG, Germany). The mechanical pump device 40 comprises a syringe pump 41 with a pump actuator 42. The syringe pump 41 has a working volume of e. g. some ml. Advantageously, the components 40, 50 and 60 can be integrated into an operation platform of the droplet dispenser device 10.

The droplet dispenser device 10 comprises a dispenser head 11, which is a mechanical support for holding at least one droplet dispenser 12 with vertical orientation. The dispenser head 11 is connected with a driving device (not shown), being capable of moving the dispenser head 11 in all three spatial directions. The droplet dispenser 12 comprises a first (lower) end with the droplet dispenser tip 13 (nozzle tip 13) and an opposite (upper) end with the upper droplet dispenser junction 14. Between both ends, a dispenser reservoir with a volume of about 60 μl and a piezoelectric actuator unit for dispensing droplets with the droplet dispenser 12 are provided. The upper droplet dispenser junction 14 is connected via a system liquid line 15 with the first port of a three-way valve 61 of the valve device 60. The system liquid line 15 is e.g. a flexible tubing.

The droplet dispenser device 10 is provided with a dispenser control device 16, being configured for controlling the operation of the droplet dispenser 12. Furthermore, the dispenser control device 16 is coupled with the pump actuator 42 for controlling the operation of the syringe pump and with a valve actuator 62 for switching the liquid connections of the three-way valve 61.

With a second port of the tree-way valve 61, the syringe pump 41 of the mechanical pump device 40 is connected. As an alternative to the direct connection (as shown in FIG. 1), a coupling via a syringe pump line (not shown) can be provided.

With the third port of the three-way valve 61, the syphon pump device 50 is connected. The syphon pump device 50 comprises a system liquid reservoir 51 connected via the syphon line 52 with the third port of the three-way valve 61. The system liquid reservoir 51 includes a system liquid 53, e. g. water, into which the syphon line 52 is immersed. The system liquid reservoir 51 is a bottle, which is arranged such that the system liquid 53 is positioned below the carrier substrate 20. Accordingly, with a continuous liquid connection between a sample droplet on the carrier substrate 20 (see below) via the droplet dispenser 12, the system liquid line 15, the three-way valve 61 and the syphon line 52 to the system liquid 53, a negative pressure is applied to the sample droplet. The height H of the system liquid 53 below the surface of the carrier substrate 20 is selected in a range of e.g. 2 cm to 10 cm.

Furthermore, FIG. 1 shows the carrier substrate 20 with a hydrophobic substrate surface 21, a buffer tube 22 and a target substrate 30. The carrier and target substrates 20, 30 are shown as plane substrate plates (provided e.g. by sample pick up slides). Alternatively, well structures, e.g. a microtiter plate or a nanotiter plate, can be used as a substrate. Both of the carrier and target substrates 20, 30 can be provided by a common substrate.

In the following, the inventive method of isolating particles from a sample suspension is described with reference to the flow chart of FIG. 2, wherein some of the operational phases of the flow chart are shown in the remaining FIGS. 3 to 8.

Figure 2:
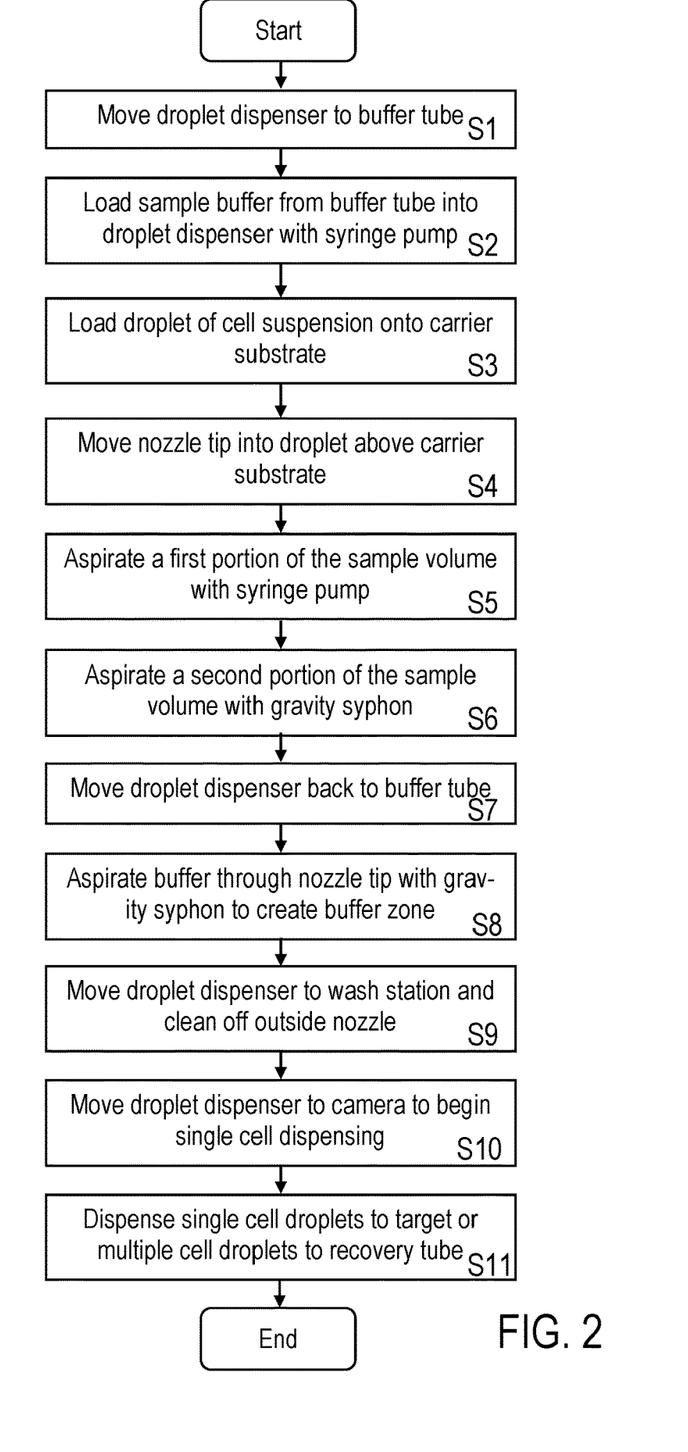
FIG. 2: a flow chart illustrating features of preferred embodiments of a method of particle isolation according to the invention.

According to FIG. 2, the illustrated embodiment of the inventive method firstly includes preparing steps S1 to S3. Firstly, the droplet dispenser 10 is moved to the buffer tube 22 (see FIG. 1), so that the droplet dispenser tip 13 (nozzle tip) is introduced into the buffer liquid within the buffer tube 22 (step S1).

Figure 3:
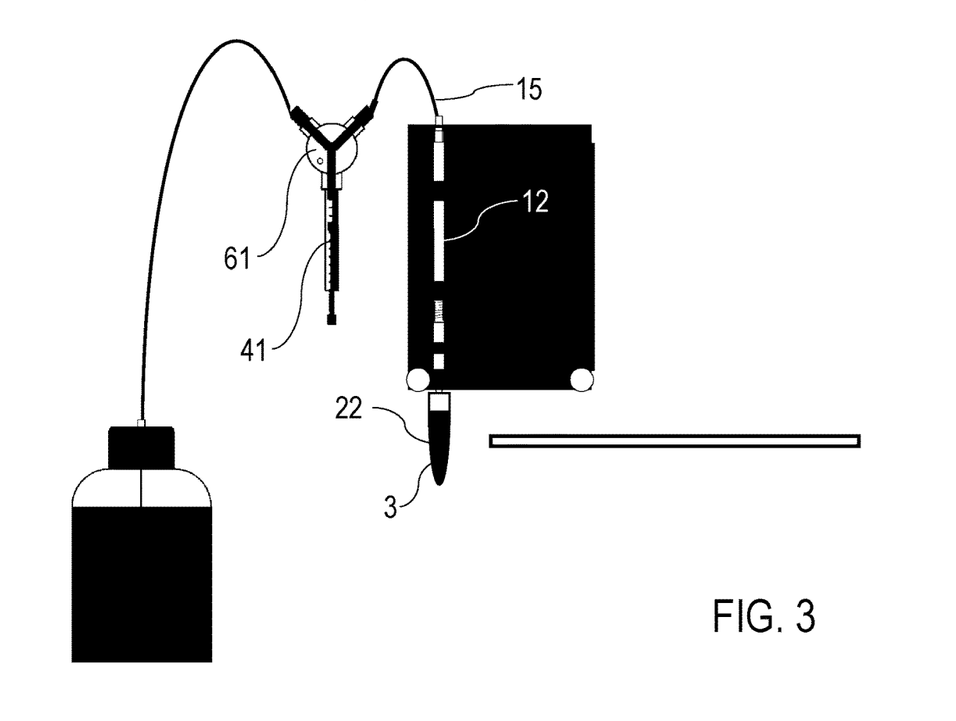
FIGS. 3 to 7: schematic illustrations of the particle isolation apparatus according to FIG. 1 in different operational phases of the particle isolation according to the invention.

Subsequently, a dilution liquid 3 (sample buffer) is loaded from the buffer tube 22 into the droplet dispenser 12 as shown in FIG. 3 (step S2). For loading the sample buffer, the three-way valve 61 is set such that the syringe pump 41 is connected via the system liquid line 15 with the droplet dispenser 12. By the action of the syringe pump 41, the sample buffer is aspirated as the dilution liquid 3 into the droplet dispenser 12. With a practical example, 20 µl of the sample buffer solution are aspirated. Advantageously, this assures that the cells accommodated from the sample suspension do not experience an osmotic shock. Furthermore, the buffer tube 22 can be used for aspirating further sample buffer to the droplet dispenser 12 after collecting the sample (formation of a buffer zone, see below). The buffer solution comprises e. g. a solvent that stabilizes the cells or particle types or a chemically similar liquid, preferably, phosphate buffered saline and/or fetal bovine serum (PBS and FBS).

Figure 4:
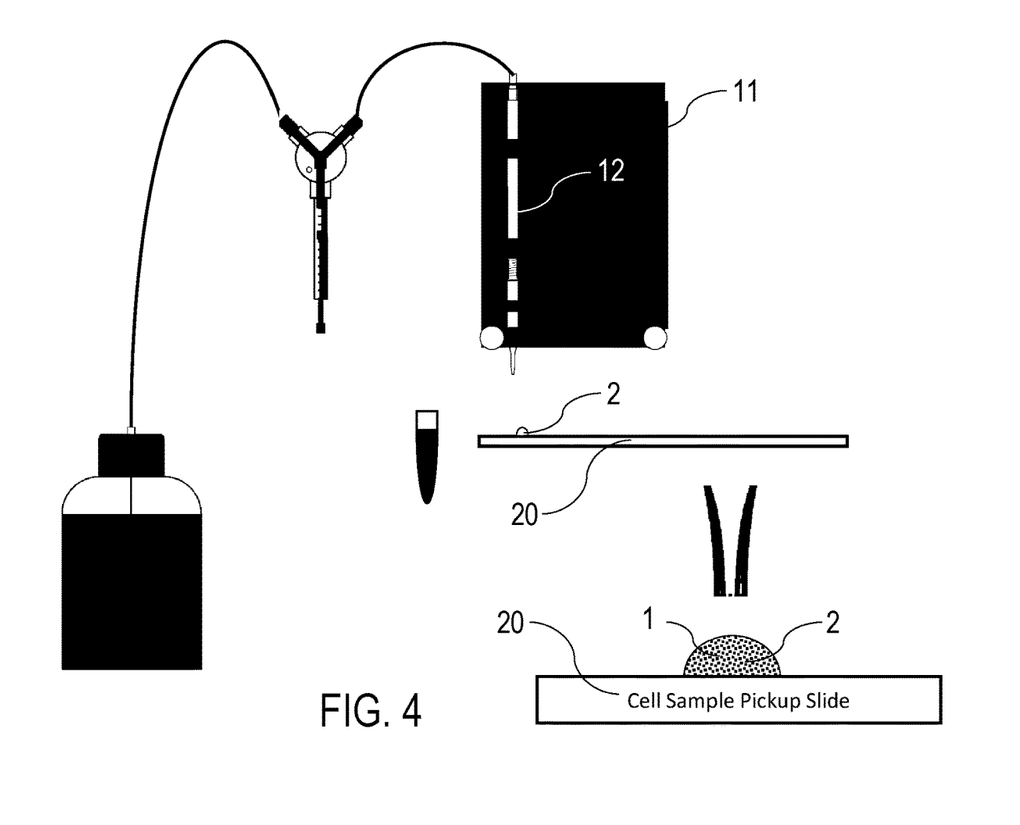

Subsequently, a droplet of a suspension sample 2 is loaded to the carrier substrate 20 and the dispenser 12 is adjusted above the droplet of the sample suspension 2 as shown in the enlarged section of FIG. 4 (step S3). The droplet of the suspension sample 2 on the carrier substrate 20 may include a plurality of particles 1, like biological cells, e. g. 100 cells or more, which are to be isolated from each other. Alternatively, the droplet may include only a few cells to be isolated from each other, or even only one cell to be recovered and transferred to the target substrate. For example, the droplet of the suspension sample 2 comprises e.g. 1 µl to 10 µl of a cell suspension containing rare cells with a density of about 1 to 30 cells per µl. Loading the droplet of the suspension sample onto the carrier substrate 20 can be conducted with another droplet dispenser (not shown) provided at the dispenser head 11, or with another liquid droplet handling technique, like i.e. a pipette or an opening of a microfluidics channel.

Figure 5:
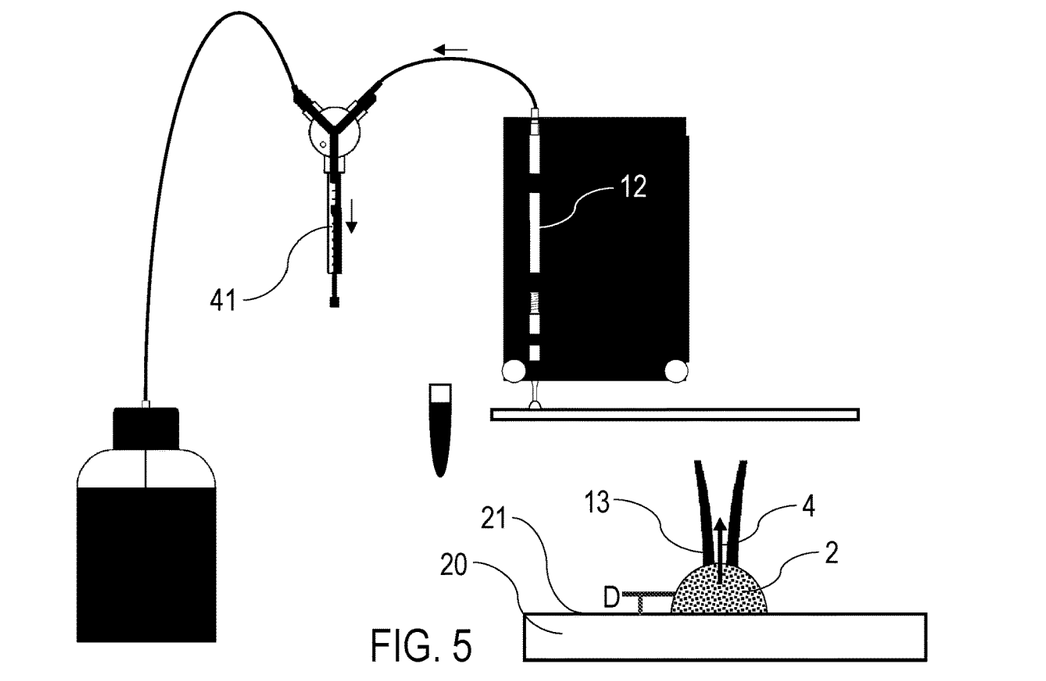
Figure 6:
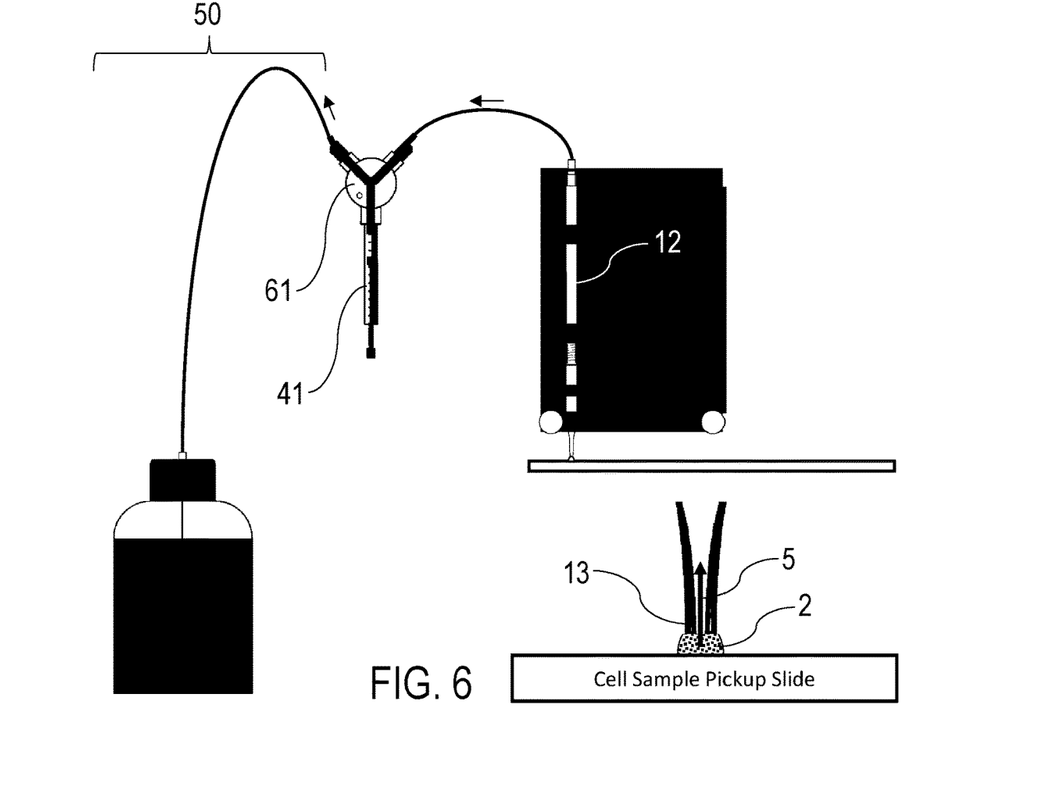

Subsequently, the droplet dispenser 12 is moved towards the carrier substrate 20 such that the nozzle tip 13 is introduced into the droplet of the suspension sample 2 as shown in FIG. 5 (step S4). According to FIG. 5 (in particular the enlarged section of FIG. 5), the nozzle tip 13 is arranged with a distance from the substrate surface 21 of the carrier substrate 20, wherein the distance is in a range from 100 µm to 250 µm. The nozzle tip 13 contacts the droplet of the suspension sample 2. Depending on the size of the droplet, the nozzle tip 13 can be submerged into the droplet down to the distance D of 100 µm.

Subsequently, the first aspiration phase is conducted, wherein a first portion 4 (see arrow) is collected via the nozzle tip 13 into the droplet dispenser 12 by the action of the syringe pump 41. The syringe pump 41 is controlled such as a predetermined volume of e.g. 2 µl is aspirated as the first portion 4 into the droplet dispenser (step S5).

Subsequently, the operation of the syringe pump 41 is stopped, and the three-way valve 61 is switched such that the first port is connected with the third port of the three-way valve 61. Accordingly, a continuous liquid connection between the syphon pump device 50 and the droplet dispenser 12 is provided (see FIG. 6). In this situation, a second portion 5 of the droplet of the suspension sample 2 is collected in a second aspiration phase by the effect of the syphon pump device 50 (step S6). Step S6 includes passive aspiration by gravity syphon to pickup remaining liquid, e. g. 2 µl. This may take 10 sec to 2 min, depending on syphon height and remaining volume. Advantageously, due to high surface tension of the system liquid and a small orifice size at the nozzle tip 13, capillary action keeps nozzle tip 13 from aspirating air. During this second aspiration phase, the complete or nearly the complete droplet of the suspension sample 2 is collected into the droplet dispenser 12.

Figure 7:
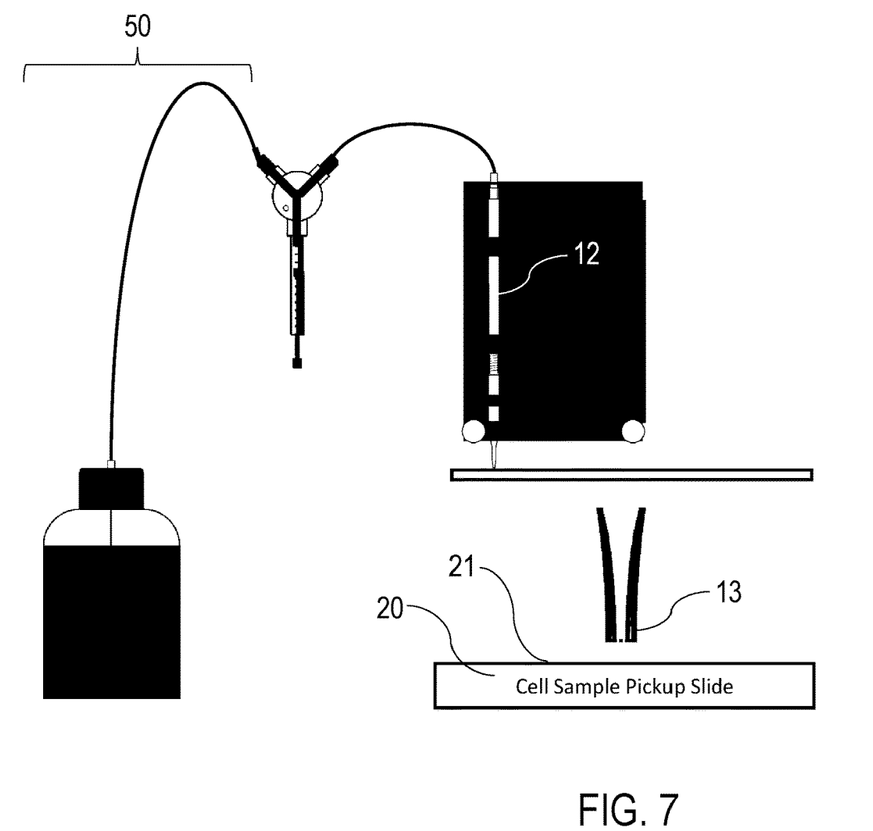

FIG. 7 shows the situation when the sample aspiration is complete. The carrier substrate 20 is empty, and the droplet of the suspension sample is completely accommodated by the droplet dispenser 12. The complete aspiration of the sample is supported by the hydrophobic surface 21 of the carrier substrate 20. Furthermore, it is preferred that the sample has a high surface tension, which is fulfilled by most of the available buffer solutions.

Subsequently, the droplet dispenser 12 is moved to the buffer tube 22 (see FIG. 1), in order to aspirate another quantity of buffer liquid through the nozzle tip 13 for creating a buffer zone within the lower end of the droplet dispenser 12 (step S8). Provision of the buffer zone in step S8 has the advantage that the suspension sample within the droplet dispenser 12 is not negatively affected by a subsequent washing step S9. The buffer liquid is aspirated into the droplet dispenser 12 by the action of the syphon pump device 50. Formation of the buffer zone may have a duration of 1 to 20 seconds.

Figure 8:
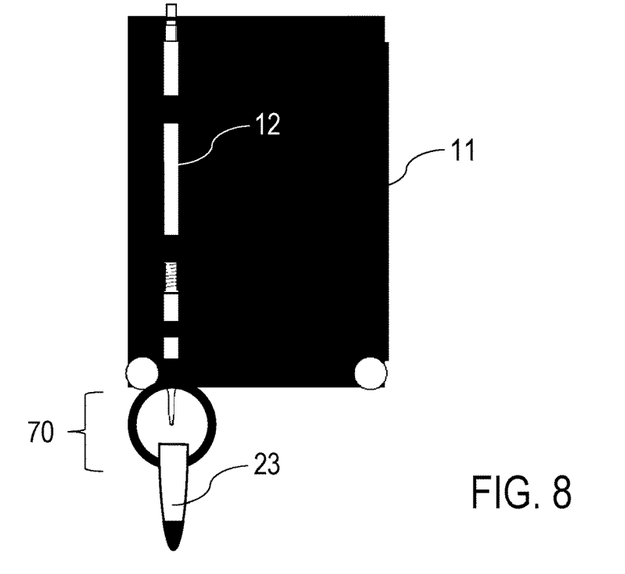
FIG. 8: a schematic illustration of recapturing multiple particle droplets.

With a next step (step S9), the droplet dispenser is moved to a wash station (not shown) for cleaning an outside surface of the nozzle 13. Subsequently, the dispenser head 11 is moved to a camera device 70 to begin with the single cell dispensing operation (step S10). With the camera device 70 and the calculation unit of the dispenser control device 16 (see FIG. 1), a distribution of the cells within the droplet dispenser 12 is evaluated. When a single cell condition of the droplet dispenser 12 is detected, e.g. as described in US 2017/0274689 A1 and EP No. 17189875.2 (not published on the priority date of the present specification) or in the references cited therein, single cell droplets are deposited on the target substrate 30 (see FIG. 1) or alternatively, if multiple cell droplets are detected, they are recaptured by a recovery tube 23 as shown in FIG. 8 (step S11).

With more details, after the sample is loaded into the droplet dispenser 12, cell detection is performed at the camera device 70. When the droplet dispenser 12 is positioned at the camera device 70, all droplets ejected from this position are captured in the recovery tube 23 located below the nozzle 13. If a single cell condition is detected, e.g. if there is one single cell in an ejection zone (corresponding to a volume ejected with one dispenser operation) and no cell is located in a sedimentation zone above the ejection zone, the droplet dispenser 12 is moved to the target substrate 30 for dispensing the next droplet including the single cell onto the target substrate 30. The sedimentation zone corresponds to a volume from which cells can sediment into the ejection zone during the movement of the dispenser device to the target substrate.

Subsequently, cell analyses can be conducted with the single cells on the target substrate 30. The cell analyses can include any cell investigation known per se, like e. g. microscopic imaging, optical, in particular fluorescence measurements, mechanical measurements, chemical sensing, etc. Depending on the result of the cell analysis, the cells can be sorted or subjected to further cell processing, like cell cultivation.

With the inventive particle isolation apparatus 100 and the above method, practical experiments have demonstrated the advantageous capability of recovery of rare cells with a recovery rate in a range from 95% to 99% or above. Initial experiments have been conducted by the inventors using fluorescently marked PBMC samples (including about 70 cells in 5 µl suspension liquid, as a model for cells of interest in autoimmune diseases. By spreading 5 µl droplets onto a substrate surface and counting the number of particles, the density of about 70 particles per 5 µl was confirmed by employing a fluorescence microscope. By applying the inventive single particle isolation, the single particles were deposited as a straight line or a matrix arrangement of particles confirming the single particle isolation capability and high recovery rate of the inventive device. An average single particle recovery of 97% was obtained.

The features of the invention disclosed in the above description, the drawings and the claims can be of significance both individually as well as in combination or sub-combination for the realization of the invention in its various embodiments.

What is claimed is:

1. A particle isolation apparatus, configured for isolating particles from a suspension sample, comprising:
    a droplet dispenser device having at least one droplet dispenser and a dispenser control device, said at least one droplet dispenser having an upper droplet dispenser junction and a droplet dispenser tip, said droplet dispenser device being configured for collecting the suspension sample from a carrier substrate through the droplet dispenser tip into the at least one droplet dispenser by an effect of a negative pressure and for dispensing droplets through the droplet dispenser tip out of the at least one droplet dispenser by an effect of a positive pressure onto a target substrate;
    a mechanical pump device being arranged to be coupled with the at least one droplet dispenser via the upper droplet dispenser junction thereof, wherein the mechanical pump device is capable of applying the positive pressure or the negative pressure to the at least one droplet dispenser; and
    a syphon pump device comprising a system liquid reservoir being arranged at a level lower than the carrier substrate and being arranged to be coupled via a continuous liquid connection with the at least one droplet dispenser via the upper droplet dispenser junction thereof,
    wherein:
    said dispenser control device is arranged for controlling operation of the at least one droplet dispenser and the mechanical pump device and for controlling coupling of the mechanical pump device and the syphon pump device with the at least one droplet dispenser, for executing the following steps:
    loading a dilution liquid with the mechanical pump device to the at least one droplet dispenser;
    loading the suspension sample to the at least one droplet dispenser, so that the suspension sample is diluted in the dilution liquid, including a first aspiration phase of aspirating a first portion of the suspension sample into the at least one droplet dispenser by action of the mechanical pump device and a second aspiration phase of aspirating a second portion of the suspension sample into the at least one droplet dispenser by action of the syphon pump device; and
    dispensing droplets with the mechanical pump device out of the at least one droplet dispenser onto the target substrate, wherein the droplets include less than one particle per droplet in a temporal average.

2. The particle isolation apparatus according to claim 1, wherein the mechanical pump device comprises a syringe pump coupled with the droplet dispenser device.

3. The particle isolation apparatus according to claim 1, further comprising a valve device configured for controlling liquid connections of at least one of the mechanical pump device and the syphon pump device with the droplet dispenser device.

4. The particle isolation apparatus according to claim 3, wherein the valve device comprises a three-way valve configured for providing a liquid connection between the mechanical pump device and the droplet dispenser device or between the syphon pump device and the droplet dispenser device.

5. The particle isolation apparatus according to claim 1, wherein the carrier substrate has a hydrophobic surface.

6. The particle isolation apparatus according to claim 1, further comprising a recovery vessel being arranged for re-capturing droplets including multiple particles.

7. The particle isolation apparatus according to claim 1, wherein the syphon pump device and the carrier substrate are configured for collecting the suspension sample in a residue-free manner.

8. A method of isolating particles from a suspension sample, comprising the steps of:
    providing the suspension sample on a carrier substrate;
    loading a dilution liquid to a droplet dispenser device;
    loading the suspension sample in the droplet dispenser device, so that the suspension sample is diluted in the dilution liquid, including a first aspiration phase of aspirating a first portion of the suspension sample into the droplet dispenser device by action of a mechanical pump device and a second aspiration phase of aspirating a second portion of the suspension sample into the droplet dispenser device by action of a syphon pump device, and dispensing droplets with the droplet dispenser device on a target substrate, wherein the droplets include less than one particle per droplet in a temporal average.

9. The method according to claim 8, comprising the further step of loading a further quantity of the dilution liquid in the droplet dispenser device after loading the suspension sample.

10. The method according to claim 8, wherein the particles comprise at least one of biological cells, cell aggregates, cell components, biological macromolecules and micro-particles functionalized with biomolecules.

11. The method according to claim 8, wherein the dilution liquid is a physiological buffer solution.

12. The method according to claim 8, further comprising at least one of the features:

the mechanical pump device comprises a syringe pump being coupled with the droplet dispenser device;

the syphon pump device comprises a system liquid reservoir arranged at a level lower than the carrier substrate and coupled with the droplet dispenser device;

liquid connections of at least one of the mechanical pump device and the syphon pump device with the droplet dispenser device are controlled with a valve device, and dispensed droplets including multiple particles are re-captured with a recovery vessel.

13. The method according to claim 12, wherein the liquid connections of at least one of the mechanical pump device and the syphon pump device with the droplet dispenser device are controlled with a three-way valve.

14. The method according to claim 8, wherein the suspension sample is collected from the carrier substrate in a residue-free manner.

* * * * *